United States Patent
Nefos et al.

(10) Patent No.: US 8,621,946 B1
(45) Date of Patent: Jan. 7, 2014

(54) SUPPORT FOR ULTRASONIC PROBE

(76) Inventors: Patrick Nefos, Fort Collins, CO (US); Chad Follmar, Louisville, CO (US)

( * ) Notice: Subject to any disclaimer, the term of this patent is extended or adjusted under 35 U.S.C. 154(b) by 254 days.

(21) Appl. No.: 13/156,032

(22) Filed: Jun. 8, 2011

(51) Int. Cl.
*G01D 21/00* (2006.01)
*A61B 8/00* (2006.01)

(52) U.S. Cl.
USPC .......................... 73/866.5; 600/459; 600/437

(58) Field of Classification Search
USPC ......... 73/866.5, 431, 661, 651, 612; 600/459, 600/446, 462–464, 437, 466–467
See application file for complete search history.

(56) References Cited

U.S. PATENT DOCUMENTS

| | | | |
|---|---|---|---|
| 4,226,229 A | 10/1980 | Eckhart | |
| 5,456,258 A | 10/1995 | Kondo | |
| 5,469,852 A * | 11/1995 | Nakamura et al. | 600/463 |
| 5,779,639 A | 7/1998 | Yeung | |
| 6,017,311 A | 1/2000 | Sakamoto | |
| 6,635,019 B2 * | 10/2003 | Davidsen | 600/459 |
| 6,733,457 B2 * | 5/2004 | Flesch et al. | 600/459 |
| 7,244,234 B2 | 7/2007 | Ridley | |
| 7,442,168 B2 * | 10/2008 | Novak et al. | 600/459 |
| 7,713,210 B2 * | 5/2010 | Byrd et al. | 600/459 |
| 8,052,607 B2 * | 11/2011 | Byrd | 600/459 |
| 8,070,685 B2 * | 12/2011 | Harhen et al. | 600/462 |
| 8,192,363 B2 * | 6/2012 | Soltani et al. | 600/439 |
| 8,246,545 B2 * | 8/2012 | Hastings et al. | 600/459 |
| 8,343,056 B2 * | 1/2013 | Baraso et al. | 600/459 |
| 2007/0129634 A1 * | 6/2007 | Hickey et al. | 600/439 |
| 2007/0208255 A1 | 9/2007 | Ridley | |
| 2007/0239022 A1 | 10/2007 | Harhen | |
| 2008/0194960 A1 | 8/2008 | Randall | |
| 2009/0281429 A1 | 11/2009 | Nishina | |
| 2010/0160788 A1 | 6/2010 | Davies | |

OTHER PUBLICATIONS

E.I. Medical Imaging, "ibex Transducers", brochure, 1 page, date unknown.
E.I. Medical Imaging, 2 pages, photos of prior product.
Repro-Scan, "Repro-Scan 200", web page www.repro-scan.com, 2 pages, copyright 2010.
BCF Technology, "Introducer", product web page www.international.bcftechnology.com/introducer, 1 page, copyright 2011.

* cited by examiner

*Primary Examiner* — Helen Kwok
(74) *Attorney, Agent, or Firm* — Jeffrey A. Proehl; Woods, Fuller, Shultz & Smith, P.C.

(57) ABSTRACT

A support for an ultrasound probe device may comprise a handle portion at a first end and providing a hand hold, with the handle portion being elongated with a first longitudinal axis. The support may comprise a pocket portion at a second end opposite of the handle portion, and which is elongated with a second longitudinal axis. The support may comprise a middle portion positioned between the handle portion and the pocket portion, with the middle portion being flexible to change and retain an angle between the first longitudinal axis and the second longitudinal axis. A cord channel may be formed in the handle portion, the pocket portion and the middle portion to receive a cord of the probe device. A probe pocket may be formed in the pocket portion to receive the probe housing of the probe device.

20 Claims, 8 Drawing Sheets

SUPPORT FOR ULTRASONIC PROBE

BACKGROUND

Field

The present disclosure relates to ultrasound probes and more particularly pertains to a new support for ultrasonic probe for providing highly configurable support of a probe.

SUMMARY

The present disclosure describes a new support for ultrasonic probe which may be utilized for providing highly configurable support of a probe that facilitates insertion of the probe in cavities of animals and particularly livestock.

In one aspect, the present disclosure relates to a support for an ultrasound probe device including a probe housing enclosing an ultrasound transducer and a cord extending from the probe housing to connect the transducer to a signal receiving unit. The support may comprise a handle portion at a first end and providing a hand hold, with the handle portion being elongated with a first longitudinal axis. The support may also comprise a pocket portion at a second end opposite of the handle portion, with the pocket portion being elongated with a second longitudinal axis. The support may also comprise a middle portion positioned between the handle portion and the pocket portion, with the middle portion being flexible to change and retain an angle between the first longitudinal axis and the second longitudinal axis. A cord channel may be formed in the handle portion, the pocket portion and the middle portion to receive a cord of the probe device. A probe pocket may be formed in the pocket portion to receive the probe housing of the probe device.

In another aspect, the present disclosure relates to an ultrasound system that may include an ultrasound probe device comprising a probe housing enclosing an ultrasound transducer and a cord extending from the probe housing for connecting the transducer to a signal receiving unit. The system may also include a support having the probe device removably mounted thereon. The support may include a handle portion at a first end and providing a hand hold, with the handle portion being elongated with a first longitudinal axis. The support may also comprise a pocket portion at a second end opposite of the handle portion, with the pocket portion being elongated with a second longitudinal axis. The support may also comprise a middle portion positioned between the handle portion and the pocket portion, with the middle portion being flexible to change and retain an angle between the first longitudinal axis and the second longitudinal axis. A cord channel may be formed in the handle portion, the pocket portion and the middle portion to receive a cord of the probe device. A probe pocket may be formed in the pocket portion to receive the probe housing of the probe device.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

With reference now to the drawings, and in particular to FIGS. 1 through 12 thereof, a new support for ultrasonic probe embodying the principles and concepts of the disclosed subject matter will be described.

Figure 12:
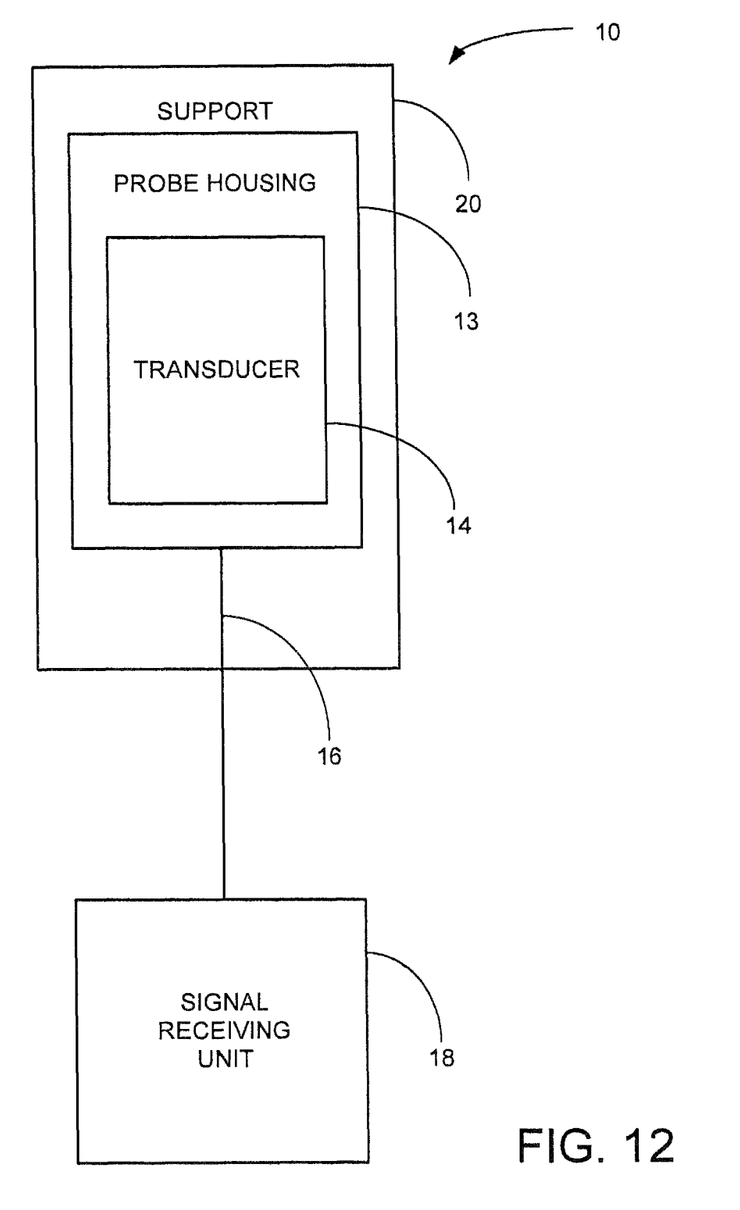
FIG. 12 is a schematic diagram of the system of the disclosure.

In one aspect, the disclosure relates an ultrasound system 10 that is useful for detecting various conditions in animals such as livestock and horses and other animals. The system may be adapted to be at least partially insertable into the rectum of a cow to detect pregnancy in the cow, although it may be employed for other uses.

The system 10 may include an ultrasound probe device 12 that may be utilized to emanate and detect ultrasonic waves. One suitable probe device is available under the tradename Ibex L6.2 transducer (part no. 290406) from E.I. Medical Imaging, 348 North Jefferson, Loveland, Colo. 80537. The probe device 12 may comprise a probe housing 13 that encloses an ultrasound transducer 14 that generates, emanates, and detects or senses the ultrasonic waves. The probe housing 13 may be relatively elongated along a longitudinal axis, and the transducer may be oriented to radiate the waves in a direction that is substantially perpendicular to the longitudinal axis of the housing. The probe device 12 may also include a cord 16 that extends from the probe housing 13 and connects the transducer to a signal receiving unit 18.

Figure 1:
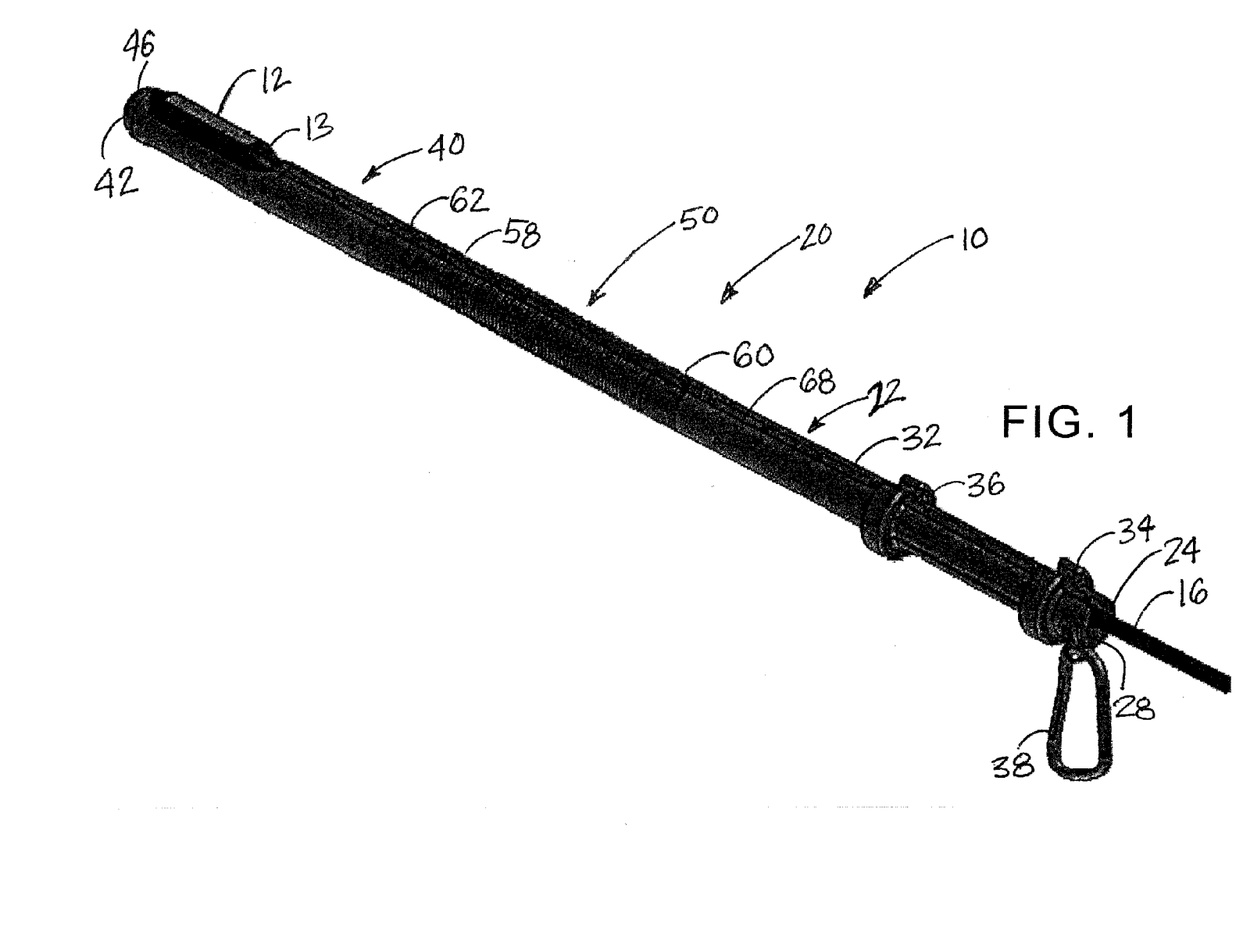
FIG. 1 is a schematic perspective view of a new ultrasound transducer device support system according to the present disclosure, and shown in a substantially straight configuration.
Figure 2:
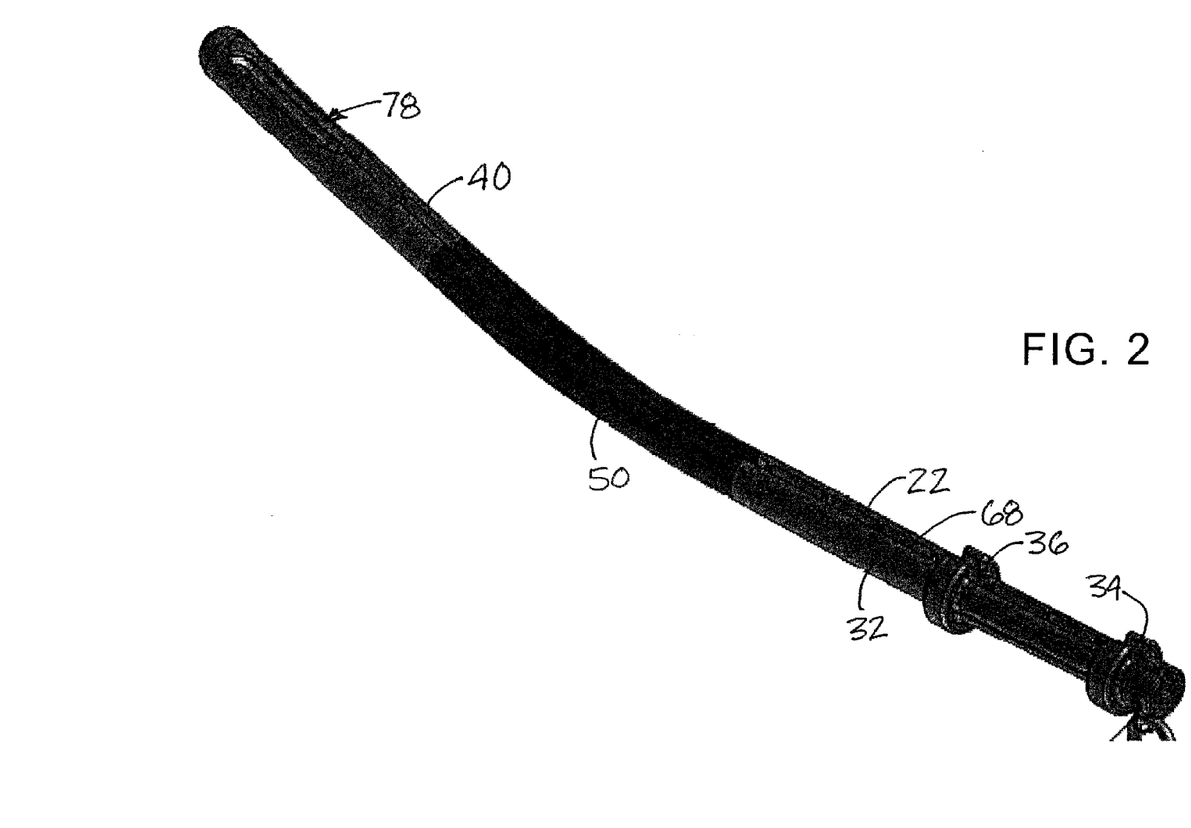
FIG. 2 is a schematic perspective view of the support according to an illustrative embodiment, and shown in a bent configuration.

A significant aspect of the system is a support 20 that may have the probe device 12 removably mounted thereon, and may be highly suitable for moving the probe device 12 into a cavity or canal of an animal. In general, the support 20 may comprise a handle portion 22, a pocket portion 40, and a middle portion 50 positioned between the handle and probe portions.

Figure 3:
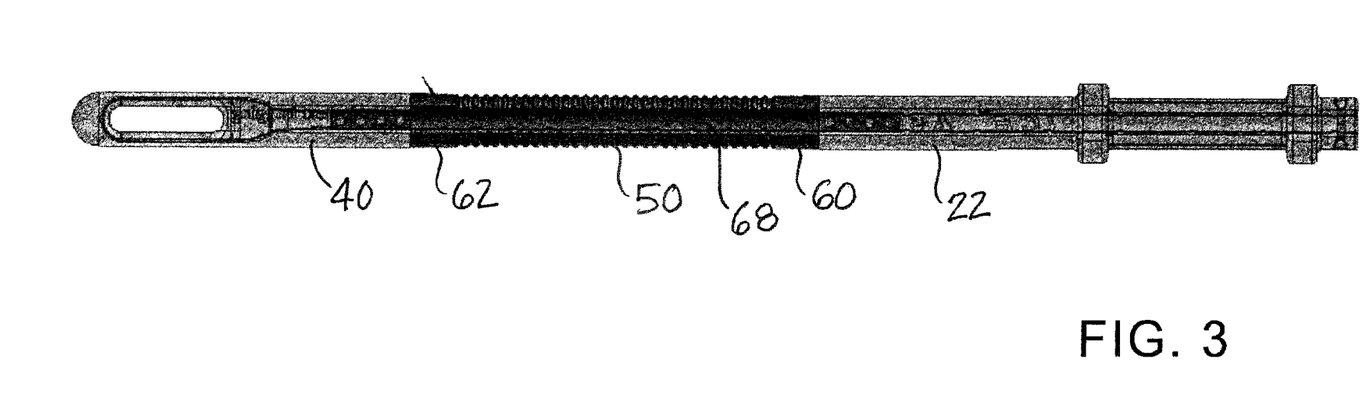
FIG. 3 is a schematic top view of the support, according to an illustrative embodiment.
Figure 4:
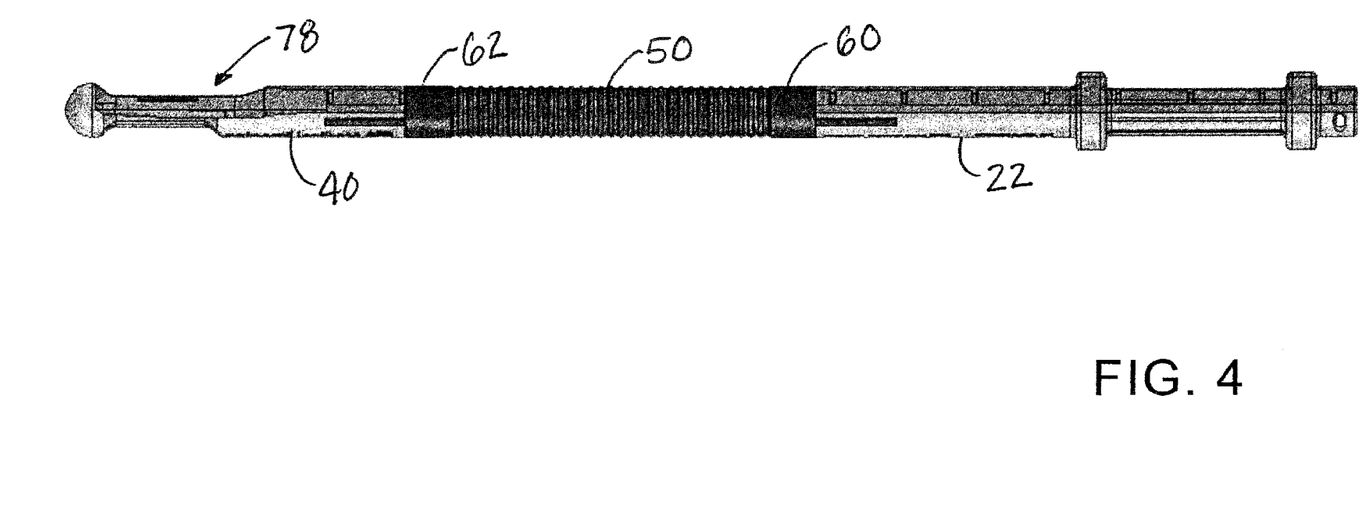
FIG. 4 is a schematic side view of the support, according to an illustrative embodiment.
Figure 5:
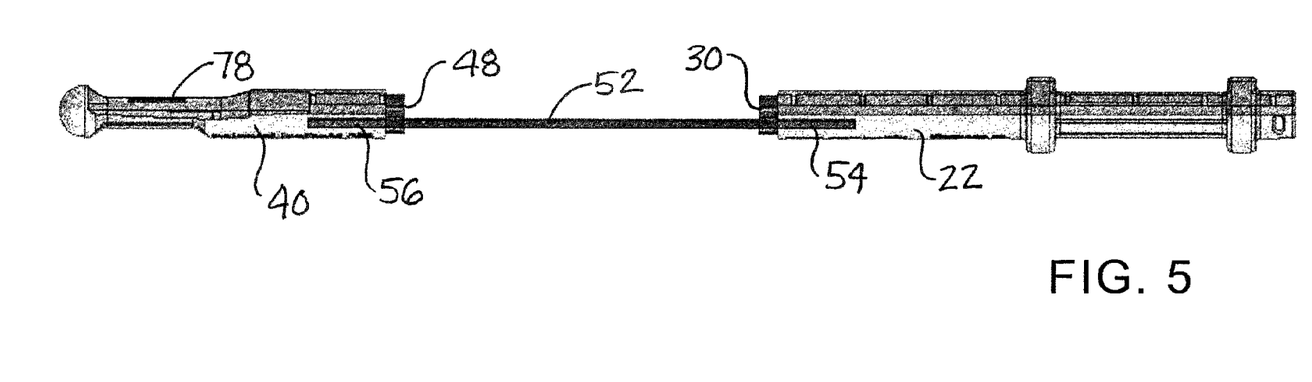
FIG. 5 is a schematic side view of the support with the sheath of the middle portion removed to exposed detail.
Figure 6:
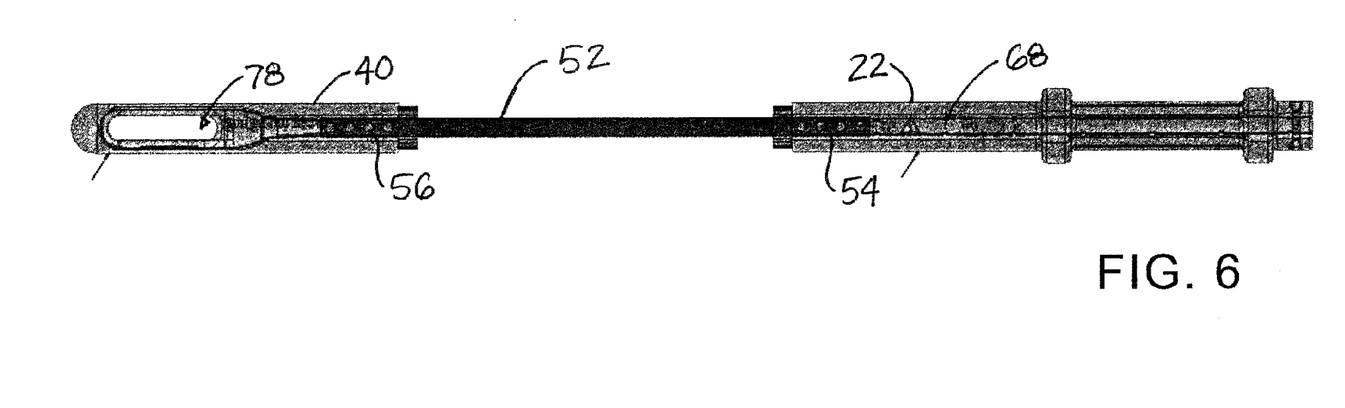
FIG. 6 is a schematic top view of the support with the sheath of the middle portion removed to exposed detail.

In greater detail, the handle portion 22 is located at a first end 24 of the support that provides a hand hold for a user of the system. The handle portion 22 may be elongated with a first longitudinal axis 26 along the length of the portion 22. The handle portion has an exterior surface which has a first end face 28 positioned on the first end 24. The handle portion 22 may extend between the end face 28 at the first end and a first intermediate end face 30.

Figure 9:
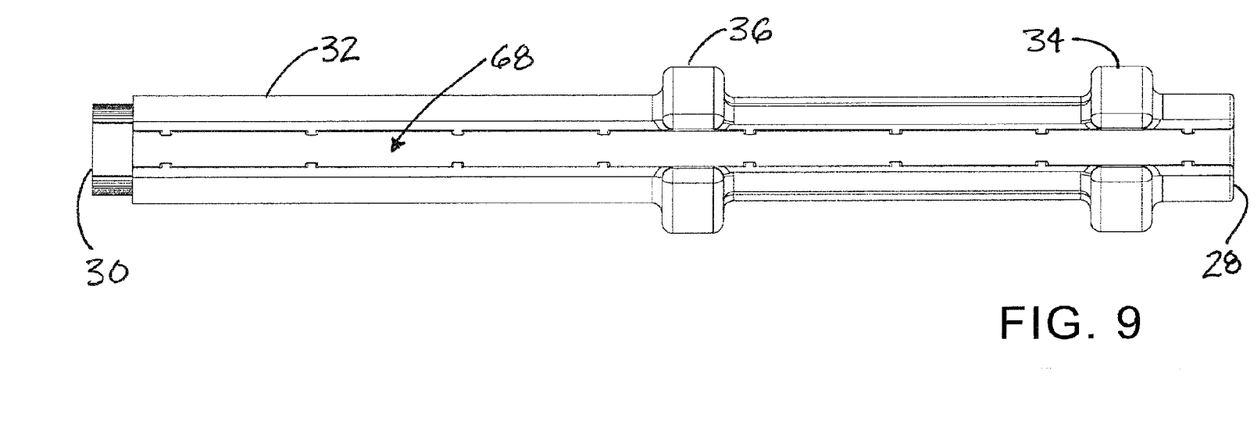
FIG. 9 is a schematic top view of the handle portion of the support showing the cord channel.

In some embodiments, the handle portion 22 comprises a central shaft 32 that extends between the first end 24 and the first intermediate end face 30, and may have a generally cylindrical exterior surface. The handle portion may also comprise at least one collar 34 that is positioned on the central shaft 32, and it may extend radially outward from the central shaft. In some embodiments, a pair of the collars 34, 36 is positioned on the central shaft and may be longitudinally spaced from each other along a length of the central shaft. The handle portion 22 may also comprise a loop 38 mounted on the central shaft 32 and may be positioned toward the first end 24. The loop 38 may be pivotally mounted on the central shaft, and may comprise a carabiner loop.

Figure 8:
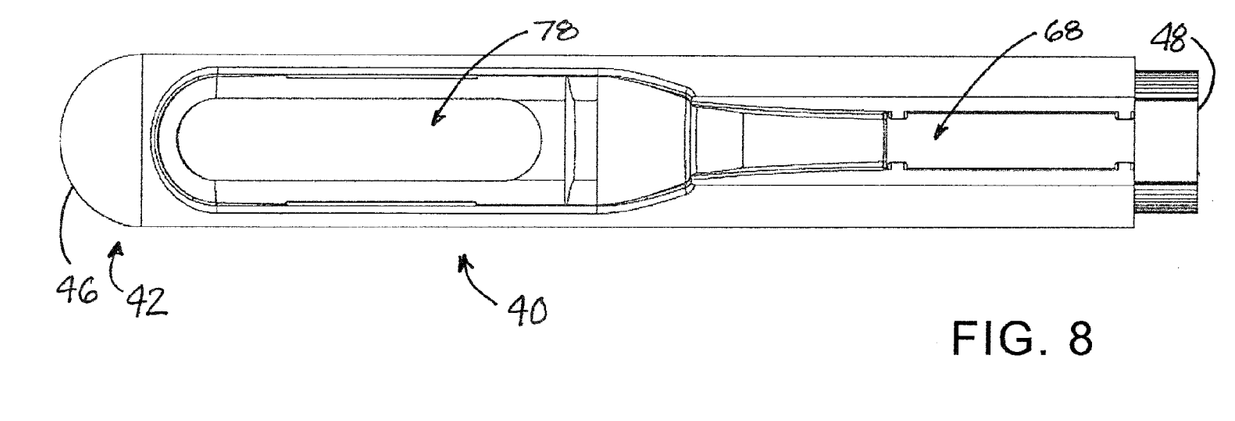
FIG. 8 is a schematic top view of the pocket portion of the support showing the probe pocket.

The pocket portion 40 of the support 29 is located at a second end 42 of the support and opposite of the handle portion 22. The pocket portion 40 may be elongated with a second longitudinal axis 44 along the length of the pocket portion. The pocket portion has an exterior surface which has a second end face 46 positioned on the second end 42. The second end face 46 may be semi-spherical in shape. The pocket portion 40 extends between the second end face at the second end and a second intermediate end face 48.

The middle portion 50 is positioned adjacent to the handle portion 22 and the pocket portion 40. The middle portion may be flexible to change and retain an angle between the first longitudinal axis 26 and the second longitudinal axis 44. The middle portion may be positioned adjacent to the first intermediate end face 30 of the handle portion and the second intermediate end face 48 of the pocket portion. The middle portion 50 may comprise a bendable core 52 that is capable of being bent by hand-applied force and retaining the bend until the further application of hand-applied force. The bendable core 52 may comprise a strap, and the strap may comprise a metal that is relatively easily bendable with the application of hand force to the strap. In some embodiments, the metal comprises copper. A first end portion 54 of the core 62 may be inserted into a cavity in the handle portion 22 and a second end portion 56 of the core may be inserted into a cavity in the pocket portion 40. The middle portion may further comprise a flexible sheath 58 that at least partially covers the core. A first end portion 60 of the sheath 58 may extend over a portion of the exterior surface of the handle portion 22 and a second end portion 62 of the sheath may extend over a portion of the exterior surface of the pocket portion 40. The sheath 58 may have an exterior surface, which may have a plurality of alternating circumferential grooves 64 and circumferential ridges 66.

Figures 10, 11:
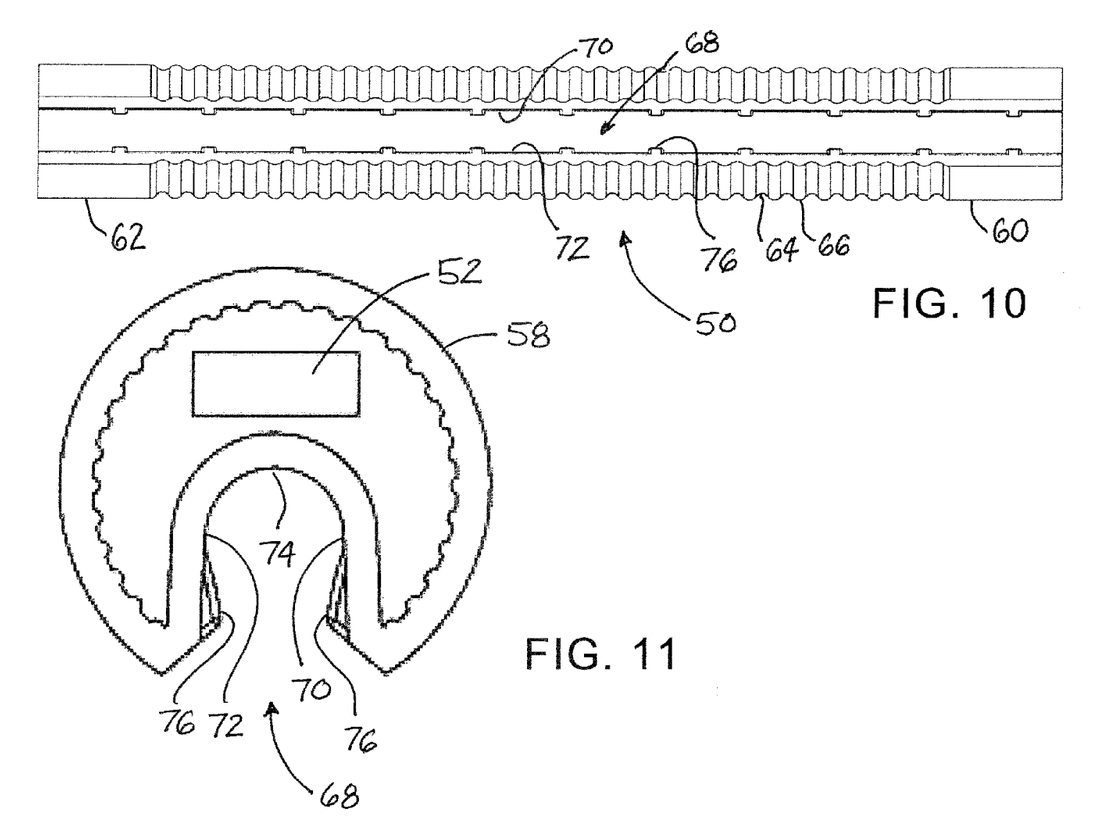
FIG. 10 is a schematic top view of the middle portion of the support showing the cord channel and protrusions.
FIG. 11 is a schematic end view of the middle portion of the support.

The support 20 may comprise a cord channel 68 that is formed in the handle portion 22, the pocket portion 40 and the middle portion 50 to removably receive a portion of the cord 16 of the probe device. In some embodiments, the cord channel 68 may comprise a pair of opposite side wall surfaces 70, 72 and a bottom wall surface 74 that extends between the side wall surfaces. The side wall surfaces may be oriented substantially parallel to each other, and the bottom wall surface may be substantially semi-cylindrical with portions that transition into the side wall surfaces. A slot may be formed by the intersection of the side wall surfaces with the respective exterior surfaces. The slot may extend along a common side of the respective portions. A plurality of cord retaining protrusions 76 may extend into the channel 68 to resist removal of the cord from the channel once the cord has been forced past the protrusions into the base of the channel. The protrusions may protrude from the side wall surfaces into the channel. The plurality of cord retaining protrusions 76 may comprise pairs of the protrusions extending from the opposite side wall surfaces and are positioned in substantial opposition to each other.

The support 20 may also comprise a probe pocket 78 that is formed in the pocket portion 40 and is configured to receive the probe housing 13 of the probe device. The pocket 78 may extend into the pocket portion from the exterior surface. The interior surface forming the probe pocket may be sized and shaped to closely fit about the probe to removably hold the probe housing in the cavity. In the illustrative embodiments, the probe pocket is elongated and rounded at the ends of the pocket. The probe pocket 78 may be in communication with the cord channel 68, and the cord channel may extend from one end of the probe pocket. In some embodiments, the probe pocket extends through the pocket portion to the opposite side of the pocket portion, so that two holes are formed.

By inclusion of the cord channel 68 and probe pocket 78, the probe device 12 may be mounted on the support 20 when the use of the support 20 is needed for the administration of an ultrasound test on an animal, such as be rectal insertion. The probe housing 13 may be inserted into the probe pocket, and the cord 16 may be inserted into the cord channel 68 along the length of the support so that the cord extends out of the first end 24 of the handle portion. After administration of the test, the probe device 12 may be removed from the support 20 by removing the probe housing from the probe pocket and the cord from the channel. The exterior surface of the portions of the support may be fabricated in a manner that is easily cleaned for repeated usages.

Figure 7:
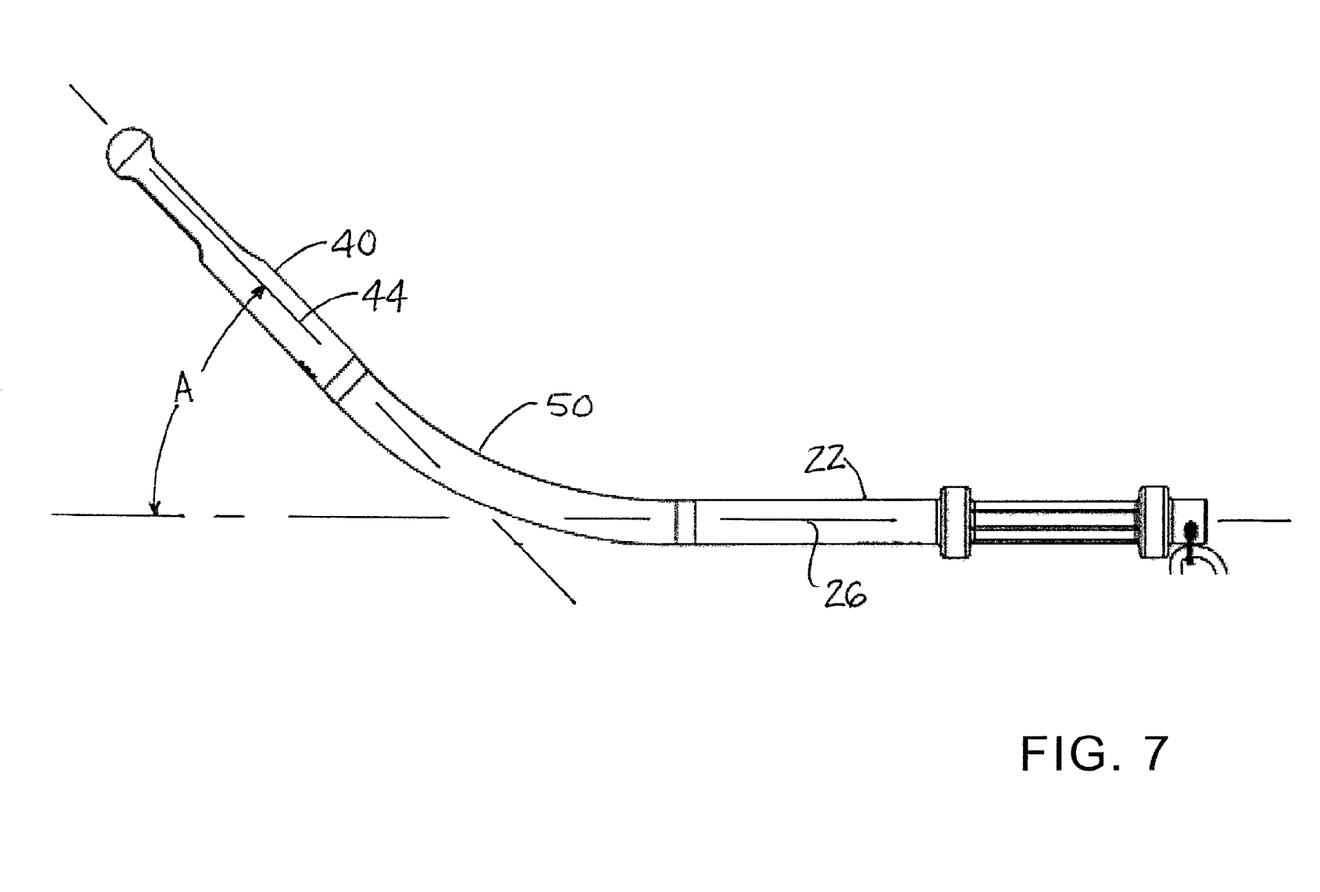
FIG. 7 is a schematic side view of the support shown with the middle portion bent to an approximately 45 degree angle.

During administration of the testing, the angle (A) between the first longitudinal axis 26 of the handle portion 22 and the second longitudinal axis 44 of the pocket portion 40 may be varied to better fit the shape of the canal into which the support 20 is to be inserted, as the shape of the canal may vary upon the species, size, and age of the animal, as well as other factors, and the user is able to vary the angle to best fit the animal. In many of the most preferred embodiments, the angle between the axes 26, 44 may be varied from approximately 0 degrees to approximately 45 degrees, although greater ranges may be utilized although this preferred range is believed to accommodate most animals. The support may subsequently be straightened out so that the axes of the handle and pocket portions are again parallel and substantially collinear.

The dimensions of the support 20 may be significant for the proper usage of the system 10, such as being large enough to accept an ultrasonic probe device 12 of the type indentified above and typically used by a veterinarian in treating animals. Thus, in some embodiments the overall length of the support from first end to second end may be suitable to reach the portions of the body of the animal with the probe housing 13 and transducer 14 for testing. Further, the support may have a major width dimension, such as a diameter, large enough to form a pocket of a size suitable to receive the probe housing 13, as well as strong and durable enough to withstand repeated insertions in a livestock confinement environment in which multiple animals my need to be serially tested. In the illustrative embodiments, the handle portion 22 have a length that is longer in length then the pocket portion, although this relationship is not critical. Illustratively, on the assembled support 20, the length of the handle portion may be approximately 13.5 inches (approximately 34 cm), the middle portion has a length of approximately 10.25 inches (approximately 26 cm), and the pocket portion has a length of approximately 8 inches (approximately 20 cm), although these parts may have different lengths when disassembled from the support.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:

1. A support for an ultrasound probe device including a probe housing enclosing an ultrasound transducer and a cord extending from the probe housing to connect the transducer to a signal receiving unit, the support comprising:
   a handle portion at a first end and providing a hand hold, the handle portion being elongated with a first longitudinal axis;
   a pocket portion at a second end opposite of the handle portion, the pocket portion being elongated with a second longitudinal axis; and
   a middle portion positioned between the handle portion and the pocket portion, the middle portion being flexible to change and retain an angle between the first longitudinal axis and the second longitudinal axis;
   wherein a cord channel is formed in the handle portion, the pocket portion and the middle portion to removably receive a cord of the probe device; and
   wherein a probe pocket is formed in the pocket portion to removably receive the probe housing of the probe device.

2. The support of claim 1 wherein the probe pocket is in communication with the cord channel.

3. The support of claim 1 wherein the cord channel comprises a pair of opposite side wall surfaces and a bottom wall surface extending between the side wall surfaces, a slot being formed by the side wall surfaces intersecting exterior surfaces of the respective portions.

4. The support of claim 1 wherein a plurality of cord retaining protrusions extend into the cord channel.

5. The support of claim 4 wherein the plurality of cord retaining protrusions comprises pairs of the protrusions in positioned in substantial opposition to each other.

6. The support of claim 1 wherein the middle portion comprises a bendable core capable of being bent by hand force applied to an exterior surface of the at least one portion of the handle, middle and pocket portions, and retaining a bend until application of hand force to the exterior surface at least one of said portions.

7. The support of claim 6 wherein the middle portion comprises a flexible sheath at least partially covering the core.

8. The support of claim 7 wherein the sheath has an exterior surface with a plurality of alternating circumferential grooves and circumferential ridges.

9. The support of claim 6 wherein the bendable core of the middle portion comprises a metal strap having a first end portion inserted into a cavity in the handle portion and a second end portion inserted into a cavity in the pocket portion.

10. The support of claim 1 wherein the handle portion comprises a central shaft extending between the first end and a first intermediate end of the handle portion, the central shaft having a generally cylindrical exterior surface; and
    at least one collar positioned on the central shaft and extending radially outward from the central shaft.

11. The support of claim 10 wherein the handle portion includes a pair of the collars longitudinally spaced along a length of the central shaft.

12. An ultrasound system, comprising:
    an ultrasound probe device comprising a probe housing enclosing an ultrasound transducer and a cord extending from the probe housing for connecting the transducer to a signal receiving unit; and
    a support having the probe device removably mounted thereon, the support comprising:
       a handle portion at a first end and providing a hand hold, the handle portion being elongated with a first longitudinal axis;
       a pocket portion at a second end opposite of the handle portion, the pocket portion being elongated with a second longitudinal axis; and
       a middle portion positioned between the handle portion and the pocket portion, the middle portion being flexible to change and retain an angle between the first longitudinal axis and the second longitudinal axis;
       wherein a cord channel is formed in the handle portion, the pocket portion and the middle portion and removably receives the cord of the probe device; and
       wherein a probe pocket is formed in the pocket portion and removably receives the probe housing of the probe device.

13. The system of claim 12 wherein the probe pocket is in communication with the cord channel.

14. The system of claim 12 wherein the cord channel comprises a pair of opposite side wall surfaces and a bottom wall surface extending between the side wall surfaces, a slot being formed by the side wall surfaces intersecting exterior surfaces of the respective portions.

15. The system of claim 12 wherein a plurality of cord retaining protrusions extend into the cord channel.

16. The system of claim 12 wherein the middle portion comprises a bendable core capable of being bent by hand-applied force and retaining a bend until application of hand-applied force.

17. The system of claim 16 wherein the middle portion comprises a flexible sheath at least partially covering the core.

18. The system of claim 17 wherein the sheath has an exterior surface with a plurality of alternating circumferential grooves and circumferential ridges.

19. The support of claim 1 wherein the middle portion has an exterior surface forming the cord channel which is accessible through an open slot.

20. A support for an ultrasound probe device including a probe housing enclosing an ultrasound transducer and a cord extending from the probe housing to connect the transducer to a signal receiving unit, the support comprising:

a handle portion at a first end and providing a hand hold, the handle portion being elongated with a first longitudinal axis;

a pocket portion at a second end opposite of the handle portion, the pocket portion being elongated with a second longitudinal axis; and a middle portion positioned between the handle portion and the pocket portion, the middle portion being flexible to change and retain an angle between the first longitudinal axis and the second longitudinal axis;

wherein the middle portion includes a sheath with an exterior surface, the exterior surface of the sheath forming an open cord channel extending into the middle portion through a longitudinal slot in a manner configured to removably receive a cord of the probe device; and wherein the pocket portion includes an open probe pocket formed by an interior surface extending from the exterior surface into the probe pocket in a manner configured to removably receive the probe housing of the probe device; and wherein the probe pocket is in communication with the cord channel such that the probe housing and the cord are removably embeddable in the pocket and middle portions.

* * * * *